United States Patent [19]

Guskey et al.

[11] Patent Number: 5,776,494
[45] Date of Patent: Jul. 7, 1998

[54] PHARMACEUTICALS COMPOSITIONS CONTAINING GELLANTS IN THE FORM OF ALKYL AMIDES OF DI-AND TRI-CARBOXYLIC ACIDS

[75] Inventors: Gerald John Guskey, Montgomery; Raymond Joseph Lo; David Frederick Swaile, both of Cincinnati, all of Ohio

[73] Assignee: The Procter & Gamble Company, Cincinnati, Ohio

[21] Appl. No.: 771,101

[22] Filed: Dec. 20, 1996

[51] Int. Cl.$^6$ ............................. A61K 9/10; A61K 47/18
[52] U.S. Cl. .................... 424/484; 424/DIG. 5; 514/944; 252/315.2
[58] Field of Search .................... 424/486, 484, 424/DIG. 5; 514/944; 252/315.2

[56] References Cited

U.S. PATENT DOCUMENTS

| | | | |
|---|---|---|---|
| 2,890,987 | 6/1959 | Hilfer | 167/90 |
| 2,900,306 | 8/1959 | Slater | 167/90 |
| 3,255,082 | 6/1966 | Barton | 167/90 |
| 3,792,068 | 2/1974 | Luedders | 260/429.3 |
| 3,887,692 | 6/1975 | Gilman | 423/462 |
| 3,903,258 | 9/1975 | Siegal | 424/66 |
| 3,904,741 | 9/1975 | Jones et al. | 423/66 |
| 3,969,087 | 7/1976 | Saito et al. | 44/7 C |
| 3,970,748 | 7/1976 | Mecca | 424/68 |
| 3,979,510 | 9/1976 | Rubino | 424/47 |
| 3,981,896 | 9/1976 | Pauling | 260/429 |
| 4,017,599 | 4/1977 | Rubino | 424/47 |
| 4,049,792 | 9/1977 | Eisnau | 424/66 |
| 4,053,581 | 10/1977 | Pader et al. | 424/68 |
| 4,126,679 | 11/1978 | Davy et al. | 424/66 |
| 4,137,306 | 1/1979 | Rubino | 424/68 |
| 4,147,766 | 4/1979 | Kozischek | 424/14 |
| 4,151,272 | 4/1979 | Geary | 424/68 |
| 4,154,816 | 5/1979 | Roehl et al. | 424/68 |
| 4,202,879 | 5/1980 | Shelton | 424/66 |
| 4,226,889 | 10/1980 | Yuhas | 424/59 |
| 4,371,645 | 2/1983 | Mahaffey, Jr. | 524/108 |
| 4,425,328 | 1/1984 | Nabial | 424/108 |
| 4,429,140 | 1/1984 | Murial et al. | 549/370 |
| 4,518,582 | 5/1985 | Schamper et al. | 424/66 |
| 4,639,369 | 1/1987 | Ciaudelli | 424/59 |
| 4,719,102 | 1/1988 | Randhawa et al. | 424/66 |
| 4,722,835 | 2/1988 | Schamper et al. | 424/66 |
| 4,725,430 | 2/1988 | Schamper et al. | 424/66 |
| 4,725,432 | 2/1988 | May | 424/66 |
| 4,743,444 | 5/1988 | McCall | 424/66 |
| 4,781,917 | 11/1988 | Luebbe et al. | 424/65 |
| 4,816,261 | 3/1989 | Luebbe et al. | 424/65 |
| 4,822,602 | 4/1989 | Sabatelli | 424/65 |
| 4,822,603 | 4/1989 | Faris et al. | 424/66 |
| 4,944,937 | 7/1990 | McCall | 424/65 |
| 4,944,938 | 7/1990 | Potini | 424/68 |
| 4,948,578 | 8/1990 | Burger et al. | 424/68 |
| 4,980,156 | 12/1990 | Raleigh et al. | 424/66 |
| 4,985,238 | 1/1991 | Tanner et al. | 424/66 |
| 4,987,243 | 1/1991 | Kawam et al. | 556/27 |
| 5,019,375 | 5/1991 | Tanner et al. | 424/66 |
| 5,023,354 | 6/1991 | Salome et al. | 549/364 |
| 5,102,656 | 4/1992 | Kasat | 424/66 |
| 5,106,999 | 4/1992 | Gardlik et al. | 549/364 |
| 5,156,834 | 10/1992 | Beckmeyer et al. | 424/47 |
| 5,169,626 | 12/1992 | Tanner et al. | 424/66 |
| 5,200,174 | 4/1993 | Gardlik et al. | 424/66 |
| 5,232,689 | 8/1993 | Katsoulis et al. | 424/66 |
| 5,346,694 | 9/1994 | Juneja | 424/66 |
| 5,384,117 | 1/1995 | Vu et al. | 424/66 |
| 5,429,816 | 7/1995 | Hofrichter et al. | 424/66 |
| 5,449,511 | 9/1995 | Coe | 424/66 |
| 5,455,026 | 10/1995 | Bahr et al. | 424/65 |
| 5,480,637 | 1/1996 | Smith | 424/78.02 |
| 5,486,566 | 1/1996 | Katsoulis et al. | 524/773 |
| 5,492,691 | 2/1996 | Bahr et al. | 404/65 |
| 5,500,209 | 3/1996 | Ross et al. | 424/66 |
| 5,516,511 | 5/1996 | Motley et al. | 424/65 |
| 5,531,986 | 7/1996 | Shevade et al. | 424/68 |
| 5,552,136 | 9/1996 | Motley | 424/68 |

FOREIGN PATENT DOCUMENTS

| | | | |
|---|---|---|---|
| 1266003 | 4/1986 | Canada | A61K 7/32 |
| 2054478 | 5/1992 | Canada | A61K 7/32 |
| 0 295 070 | 12/1988 | European Pat. Off. | A61K 7/32 |
| 0 295 071 | 12/1988 | European Pat. Off. | A61K 7/32 |
| 0 396 137 | 11/1990 | European Pat. Off. | A61K 7/32 |
| 0 448 278 | 9/1991 | European Pat. Off. | A61K 7/38 |
| 530866 A1 | 3/1993 | European Pat. Off. | A61K 7/48 |
| 0 616 842 A1 | 9/1994 | European Pat. Off. | B01J 13/00 |
| 0 682 940 A1 | 11/1995 | European Pat. Off. | A61K 7/48 |
| A61 206 450 | 9/1986 | Japan | A61L 9/01 |
| A62 265393 | 11/1987 | Japan | C10L 3/00 |
| A10 20286 | 1/1989 | Japan | C09K 3/00 |
| 1-207223 | 8/1989 | Japan | A61K 7/02 |
| 2-180805 | 7/1990 | Japan | A61K 7/00 |
| 2-264707 | 10/1990 | Japan . | |
| 3-170415 | 7/1991 | Japan | A61K 7/32 |
| A 42 08 202 | 7/1992 | Japan | A01N 25/18 |
| 1485694 | 9/1977 | United Kingdom | B01F 17/28 |
| 2253347 | 9/1992 | United Kingdom | A61K 7/32 |
| 2299024 | 9/1996 | United Kingdom | A61K 7/32 |
| WO 96/26709 | 9/1996 | WIPO | A61K 7/32 |

OTHER PUBLICATIONS

M. F. Bobin, C. Suzza and M–C. Martini, "Using Fluorinated Compounds in Topical Preparations", 111 *Cosmetics and toiletries* 47–63, Oct., 1996.

Taro Tachibana and Hideko Kambara, "Studies of Helical Aggregates of Molecules. I. Enantiomorphism in the Helical Aggregates of Optically Active 12–Hydroxystearic Acid and Its Lithium Salt", *Bulletin of the Chemical Society of Japan*, vol. 42, 3422–3424 (1969).

(List continued on next page.)

Primary Examiner—Edward J. Webman
Attorney, Agent, or Firm—Tara M. Rosnell; Darryl C. Little

[57] ABSTRACT

The present invention relates to pharmaceutical compositions useful as carriers for topical skin actives such as moisturizers, protectants, antiperspirants, deodorants and the like; and more particularly, to such pharmaceutical compositions in the form of a gel or gel stick.

20 Claims, No Drawings

OTHER PUBLICATIONS

Taro Tachibana, Shyoko Kitazawa and Hideko Takeno, "Studies of Helical Aggregates of Molecules. II, The Sense of Twist in the Fibrous Aggregates from the Alkali Metal Soaps of Optically Active 12–HydroxystearicAcid", *Bulletin of the Chemical Society of Japan*, vol. 43 2418–2421 (1970).

"Electron Microscopic and Thermal Studies of Optically Active 12–Hydroxystearic Acids in Soap Formation", *Journal of colloid and Interface Science*, vol. 51, No. 2, May 1975.

"Morphology of Collapsed Monolayers of Optically Active and Racemic 12–Hydroxystearic Acids", *Journal of Colloid and Interface Science*, vol. 61, No. 2, Sep. 1977.

C. D. Vaughn, "Solubility Effects in Product, Package, Penetration and Preservation" 103 *Cosmetics and Toiletries* 47–69, Oct. 1988.

Plechner, *Antiperspirants and Deodorants*, 2 Cosmetics, Science and Technology, Balsam and Sagarin, 374–400, 1972.

C. D. Vaughn, "Using Solubility Parameters in Cosmetics Formulation", 36 *J. Soc. Cosmetic Chemists* 319–333 Sep./Oct., 1985.

Tsau, Heller and Pratap, "Thermoreversible Organogels of 12–Hydroxystearic Acid", *Polymer Preprints* 1994, 35, 737–738.

Balsam and Sagarin, Cosmetics, Science, and Technology, vol. 1, 27–104, 1972.

Geria, "Formulation of Stick Antiperspirants and Deodorants", *Cosmetics and Toiletries*, 99:55–60 (1984).

Gel and Sticks Formulary, 99 *Cosmetics and Toiletries* 82–87, 1984.

Todd et al., "Volatile Silicone Fluids for Cosmetics", *Cosmetics and Toiletries*, 91:29–32 (1976).

Chemical Abstracts, vol. 85, No. 2, Jul. 12, 1976 No. 85:10310.

Taro Tachibana, Tomoko Mori and Kayako Hori, "New type of twisted mesophase in jellies and solid films of chiral 12–hydroxyoctadecanoic", *Nature*, vol. 278, Apr. 1979.

Tachibana, Mori and Hori, "Chiral Mesophases of 12–Hydroxyoctadecanoic Acid in Jelly and in the Solid State. II. A new Type of Mesomorphic Solid State", *Bulletin of the Chemical Society of Japan*, vol. 54, 73–80 (1981).

Ito, Yudasaka and Fujtyama, "Light Scattering Study of the 12–Hydroxyoctadecanoic Acid and Benzane Mixture in the Gel State", *Bulletin of the Chemical Society of Japan*, vol. 54, 1939–1942 (1981).

Tamura, Suetake, Ohkubo and Ohbu, "Effects of Alkali Metal Ions on Gel Formation in the 12–Hydroxystearic Acid/Soybean Oil System", *JAOCS*, vol. 71, No. 8 (Aug. 1994).

Cebula and Smith, "Differential Scanning Calorimetry of Confectionery Fats. Pure Triglycerides: Effects of Cooling and Heating Rate Variation", *JAOCS*, vol. 68 No. 8 (Aug. 1991).

Taro Tachibana, Tomoko Mori, and Kayako Hori, "Chiral Mesophases of 12–Hydroxyoctadecanoic Acid in Jelly and in the Solid State. I. A New Type of Lyotropic Mesophase in Jelly with Organic Solvents", *Bulletin of the Chemical Society of Japan*, vol. 53, No. 6, 1714–1719 (1980).

PHARMACEUTICALS COMPOSITIONS CONTAINING GELLANTS IN THE FORM OF ALKYL AMIDES OF DI-AND TRI-CARBOXYLIC ACIDS

FIELD OF THE INVENTION

The present invention relates to compositions useful as carriers for pharmaceutical actives such as antiseptics, antifungals, suncreens, deodorants and the like; and more particularly, to such pharmaceutical compositions in the form of a gel or gel stick.

BACKGROUND OF THE INVENTION

Pharmaceutical actives effective topically in treating dermatological conditions are generally delivered by means of ointment, gel, gel solids, lotion or cream vehicles. Such vehicles provide varying degrees of emolliency and barrier protection for the skin, thus promoting uniform application and effective transdermal absorption of the actives. Conventional examples of such vehicles are described in Sagarin, Cosmetics Science and Technology, 2nd Edition, Vol. 1, Wiley Interscience (1972) and Encyclopedia of chemical Technology, Third Edition, Volume 7. In recent years, gel solid vehicles have become increasingly popular in view of their easy "no touch" form of application as well as the discovery of lower visible residue formulations.

The stick form is distinguished from gels or pastes in that the stick can maintain its shape for extended time periods outside the package (although some shrinkage occurs due to solvent evaporation). Alternatively, one can adjust the amount of stearyl alcohol and castor wax and/or modify the manufacturing process to produce a viscous gel or paste in place of the stick. These gels or pastes can be suitably packaged in containers which have the appearance of a stick, but which dispense through apertures on the top surface of the package. These products are typically called soft sticks or "smooth-ons". A more detailed description of soft gels is found in U.S. Pat. No. 5,102,656 to Kasat, U.S. Pat. No. 5,069,897 to Orr, and U.S. Pat. No. 4,937,069 to Shin, each of which are herein incorporated by reference in their entirety.

As alluded to above, however, an important disadvantage of hard gel stick carriers remains the visible residue associated with their application. This visible residue tends to stain fabrics and is, therefore, considered undesirable by consumers. Furthermore, in formulating gel stick carriers, the active ingredients are typically suspended in a vehicle such as cyclomethicone. Such suspensions generally result in syneresis and/or weeping problems which adversely affect formula stability and aesthetic properties; this is particularly true when shipping in warm climates and/or high altitudes.

Attempting to address these concerns, researchers have suggested varying the type of gelling agent used. One proposal involved the use of dibenzylidene alditols. One problem with Dibenzylidene alditols, however, relates to its inherent instability in acidic environments. Moreover, gel solid sticks which combined such gelling agents with certain actives (e.g., solubilized antiperspirant actives) resulted in gel solid sticks having a tacky skin feel.

Another attempt involved the use of n-acyl amino acid gelling gents. Information regarding the use of these gelling agents is found in: U.S. Pat. No. 3,969,087 issued on Jul. 13, 1976 to Saito et al.; Japanese Patent Application 1-207223, published Aug. 21, 1989; Japanese Patent Application 1-207223 which published Aug. 21, 1989; and Japanese Patent Application 2-180805 which published Jul. 13, 1988.

While the prior art discloses a variety of gelling agents useful in formulating soft gel or gel stick compositions, there is still a need for additional formulations which reduce the visible residue associated with such compositions. The present inventors have found that soft gel or gel stick pharmaceutical compositions that incorporate gelling agents in the form of alkyl amides of di- and tri-basic carboxylic acids provide such reduced visible residue compositions.

Accordingly, it is an object of the present invention to provide improved pharmaceutical compositions.

It is also an object of the present invention to provide improved pharmaceutical compositions in the form of a gel or gel solid stick.

It is another object of the present invention to provide improved gel solid stick or soft gel pharmaceutical compositions further comprising a pharmaceutically acceptable active.

It is a further object of the present invention to provide improved gel solid stick or gel pharmaceutical compositions for topical application to mammalian skin or mucous tissue, containing a pharmaceutically acceptable active and gelling agent, having good structural integrity with reduced visible residue.

A still even further object of the present invention to provide methods for delivering pharmaceutically acceptable actives.

These and other objects will become readily apparent from the disclosure which follows.

SUMMARY OF THE INVENTION

The present invention relates to pharmaceutical compositions, comprising:

A.) a safe and effective amount of at least one pharmaceutical active;

B.) a gelling agent of the formula:

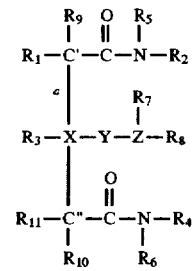

a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl;

g) X is nil, nitrogen, aryl or $-(CH_2)_n$ where n is an integer from 1 to 6;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl; and j) "a" is a double or single bond provided:
   (i) when X is nil, Y, Z, $R_3$, $R_7$ and $R_8$ are nil, C' is bonded directly to C" and $R_1$ is not a hydrogen;
   (ii) when X and Z are not nil and Y is nil, X is directly bonded to Z;
   (iii) when Z is nil, a hydrogen or a hydroxy, $R_7$ and $R_8$ are nil; and
   (iv) when "a" is a double bond, $R_3$ and $R_9$ are nil; and C.) an anhydrous liquid carrier.

The present invention further relates to methods for delivering skin pharmaceutical materials and actives with reduced residue.

By "acyl" or "carbonyl" as used herein, means a radical formed by removal of the hydroxy and alkyl portions of a carboxylic acid (i.e.

By "alkyl" as used herein, means an unsubstituted or substituted saturated hydrocarbon chain radical having from 1 to 22 carbon atoms, preferably from 1 to 8 carbon atoms. Preferred alkyl groups include, but are not limited to, methyl, ethyl, propyl, isopropyl, butyl, hexyl and octyl.

By "alkenyl" as used herein, means an unsubstituted or substituted hydrocarbon chain radical having from 2 to 22 carbon atoms, preferably from 2 to 8 carbon atoms, and having at least one olefinic double bond.

By "aryl" as used herein, means an aromatic carbocyclic ring radical. Preferred aryl groups include, but are not limited to, phenyl, tolyl, xylyl, cumenyl and naphthyl.

By "alkoxy" as used herein, means an oxygen radical having a hydrocarbon chain substituent, where the hydrocarbon chain is an alkyl or alkenyl (i.e., —O—alkyl or —O—alkenyl). Preferred alkoxy groups include, but are not limited to, methoxy, ethoxy, propoxy and allyloxy.

By "siloxane" as used herein, means a linear compound consisting of silicon atoms single-bonded to oxygen and so arranged that each silicon atom is linked with two or four oxygen atoms (i.e., —Si(O)$_2$RR' where R and R', independently, are, but not limited to, alkyls, alkyl esters or alkyl ethers).

By "cyclic chain" as used herein, means an unsubstituted or substituted, saturated, unsaturated or aromatic, hydrocarbon chain ring radical. The cyclic chains are monocyclic or are fused, bridged or spiro polycyclic ring systems.

As defined above and as used herein, substituent groups may themselves be substituted. Such substitution may be with one or more substituents. Such substituents include (for example) those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

All levels and ratios are by weight of the total composition, unless otherwise indicated. Additionally, all measurements are made at 25° C. unless otherwise specified. By the phrase "ambient temperature" as used herein, refers to surrounding conditions under about one atmosphere of pressure, at about 50% relative humidity, and at about 25° C., unless otherwise specified.

The pharmaceutical compositions of the present invention can comprise, consist of, or consist essentially of the essential elements and limitations of the invention described herein, as well as any of the additional or optional ingredients, components, or limitations described herein.

DETAILED DESCRIPTION OF THE INVENTION

The essential as well as optional components of the compositions of the present invention are described in the following paragraphs.

ESSENTIAL COMPONENTS
Pharmaceutically Acceptable Active

An essential component of the present invention are the pharmaceutically acceptable actives. By the phase "pharmaceutically acceptable active", as used herein means actives topically administered to skin or mucosal tissue as a form of treatment or to produce a benefit. Such actives include, but are not limited to, antiseptic or antibacterial, antifungals, exfoliating agents, topical NSAIDS, sunscreens, antidandruff agents, deodorants, antiperspirants, and the like. The phrase "safe and effective amount", as used herein, means an amount of an active high enough to significantly or positively modify the condition to be treated, but low enough to avoid serious side effects (at a reasonable benefit/risk ratio), within the scope of sound medical judgment. A safe and effective amount of the pharmaceutically acceptable active will vary with the specific active, the ability of the composition to penetrate the active through the skin, the amount of composition to be applied, the particular condition being treated, the age and physical condition of the patient being treated, the severity of the condition, the duration of the treatment, the nature of concurrent therapy, and like factors.

The pharmaceutical active of the present invention can be an antiseptic or antibacterial active. Preferred antiseptic or antibacterial actives include (but are not limited to): 2-hydroxy-4,2',4'-trichlorodiphenylether, (TCS); 2,6-dimethyl-4-hydroxychlorobenzene (PCMX);3,4,4'-trichlorocarbanilide (TCC); 3-trifluoromethyl-4,4'-dichlorocarbanilide (TFC); 2,2'-dihydroxy-3,3',5,5',6,6'-hexachlorodiphenylmethane; 2,2'-dihydroxy-3,3',5,5'-tetrachlorodipheylmethane; 2,2'-dihydroxy- 3,3', dibromo-5, 5'-dochlorodiphenylmethane; 2-hydroxy-4,4'-dichlorodiphenylether; 2-hydroxy-3,5',4-tribromodiphenylether; 1-hydroxy-4-methyl-6-(2,4,4-trimethylpentyl)-2(1H)-pyridinone (Octopirox);

nitrofurantoin; phenazopyridine; acyclovir; chlorohexidine; peroxides; benzalkonium chloride; benzathonium chloride; iodine; povidone-iodine; methylbenzethonium chloride; rapamycin derivatives and mixtures thereof.

The antiseptic or antibacterial active may be present at a concentration of from about 0.01% to about 10%, typically from about 0.1% to about 10% and preferably from about 0.5% to about 10%. The level is selected to provide the desired level of antiseptic or antibacterial activity and can be modified as desired.

The pharmaceutical agent can also be an antifungal agent. Antifungal agents suitable for use in the articles of the present invention are selected from the group consisting of butoconazole, clotrimazole, econazole, fluconazole, itraconazole, ketoconazole, miconazole, terconazole, sulconazole, nystatin, haloprogin, tolnaftate, their pharmacological salts and mixtures thereof.

Preferred for use herein are the 1-(β-aryl) ethyl-imidazole ethers and amines disclosed in U.S. Pat. No. 3,717,655 to Godefroi et al. issued Feb. 20, 1973 derivatives of substituted N-alkyl imidazoles disclosed in U.S. Pat. No. 4,078,071 to Walker, issued Mar. 7, 1978. Other preferred antimicrobials include the tin-containing polymers disclosed in U.S. Pat. No. 5,043,463 to Carraher Jr., et al., issued Aug. 27, 1991. All of these patents are incorporated by reference herein.

The antifungal agent may be present at a concentration of from about 0.01% to about 4%, typically from about 0.1% to about 2% and preferably from about 0.5% to about 2%. The level is selected to provide the desired level of antifungal activity and can be modified as desired.

Other useful components include hormones such as pregnenolone and estrogens.

Exfoliating agents such as salicylic acid and salicylic acid derivatives can be incorporated into the present invention. Also useful are the alpha-, or beta-hydroxy acids or alpha-keto acids or derivatives thereof as disclosed in U.S. Pat. No. 4,234,599 to Van Scott et al., issued Nov. 18, 1980 which is incorporated by reference herein. Useful members of this class include alpha-hydroxy-butyric acid, alpha-hydroxyisobutyric acid, alpha-hydroxyisocaproic acid, alpha-hydroxyisovaleric, atrolactic acid, beta-hydroxybutyric acid, beta-phenyl lactic acid, beta-phenylpyruvic acid, citric acid ethyl pyruvate, galacturonic acid, glucoheptonic acid, glucoheptono 1,4-lactone, gluconic acid, gluconolactone glucuronic acid, glucuronolactone, glycolic acid, isopropyl pyruvate, lactic acid, malic acid, mandelic acid, methyl pyruvate, mucic acid, pyruvic acid, saccharic acid, saccharic acid 1,4-lactone, tartaric acid and tartronic acid.

The compositions of the present invention can also include topical analgesics agents such as, but not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, arncinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, piroxicam, isoxicam, tenoxicam, sudoxicam,CP-14,304, aspirin, disalcid, benorylate, trilisate, safapryn, solprin, diflunisal, and fendosal, diclofenac, fenclofenac, indomethacin, sulindac, tolmetin, isoxepac, furofenac, tiopinac, zidometacin, acematacin, fentiazac, zomepiract, clidanac, oxepinac, and felbinac, mefenamic, meclofenamic, flufenamic, niflumic, and tolfenamic acid, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic, phenybutezone, oxyphenbutezone, feprazone, azapropezone, and trimethazone and mixtures thereof.

Sunscreen actives may also be incorporated into the present invention. Suitable sunscreen agents include, but are not limited to, p-aminobenzoic acid, its salts and its derivatives (ethyl, isobutyl, glyceryl esters; p-dimethylaminobenzoic acid); anthranilates (i.e., o-aminobenzoates; 5, methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (methyl and benzyl esters, a-phenyl cinnamonitrile; butyl cinnamoyl pyruvate); Dihydroxycinnamic acid derivatives (umbelliferone, methylumbelliferone, methylacetoumbelliferone); Trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyidisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, 2,2',4,4'-Tetrahydroxybenzophenone, 2,2'-Dihydroxy-4,4'-Benzoresorcinol, dimethoxybenzophenone, Octabenzone; 4-Isopropyidibenzoylmethane; Butyl-methoxydibenzoylmethane; Etocrylene; and 4-isopropyl-dibenzoylmethane and mixtures thereof.

The compositions of the present invention may also include anti-oxidant or radical scavengers. Suitable anti-oxidants or radical scavengers include, but are not limited to, butylated hydroxy benzoic acids, 6-hydroxy-2,5,7,8-tetramethylchroman-2-carboxylic acid, gallic acid, propyl gallate, uric acid, sorbic acid, ascorbyl esters of fatty acids, amines, sulfhydryl compounds, dihydroxy fumaric acid, pharmaceutically acceptable salts thereof, alkyl esters thereof, derivatives thereof and mixtures thereof.

The compositions of the present invention may also include topically administered vitamins. Such vitamins include, but are not limited to Vitamin A, ascorbic acid, Vitamin B, biotin, panthothenic acid, Vitamin D, Vitamin E and mixtures thereof and derivatives thereof. Derivatives or analogs of these vitamins may also be used such as synthetic Vitamin A analogs, natural Vitamin A analogs, geometric isomers and stereoisomers and mixtures thereof.

Other useful actives which are useful in the present compositions include anti-dandruff actives such as zinc pyrithione, octopirox, selenium disulfide, sulfur, coal tar, and the like.

Deodorant actives (e.g., bacteriostats, deodorant fragrances, odor absorbents, odor preventing agents, etc.) are described in the chapter entitled "Deodorant Ingredients" by E. P. Seitz, et al, in Antiperspirants and Deodorants, (K. Laden, et al Ed. 1988), pages 345–390. Antiperspirants and Deodorants is volume 7 of the Pharmaceutical Science and Technology Series. This chapter, entitled "Deodorant Ingredients" is incorporated herein by reference in its entirety. Suitable deodorant bacteriostats include 2,2'-methylenebis (3,4,6-trichlorophenol), 2,4,4'-trichloro-2'-hydroxy (diphenyl ether), zinc phenolsulfonate, 2,2'-thiobis(4,6-dichlorophenol), p-chloro-m-xylenol, dichloro-m-xylenol and the like. Most preferred is 2,4,4'-trichloro-2'-hydroxy (diphenyl ether), which is generically known as triclosan and available from the Ciba-Geigy Corporation under the trademark, Irgasan DP-300 Registered TM. When triclosan is utilized it will be present in a range from about 0.05 to about 0.9%, preferably from about 0.1 to about 0.5% by weight of the composition. Other types of bacteriostats include sodium N-lauroyl sarcosine, sodium N-palmitoyl sarcosine, lauroyl sarcosine, N-myristoyl glycine, potassium N-lauroyl sarcosine and aluminum chlorhydroxy lactate (sold by Reheis Chemical Company under trademark of Chloracel).

The compositions of the present invention can also incorporate antiperspirant actives. These antiperspirant actives are preferably particulate astringent compounds having an average particle size between about 5–200 microns. Suitable astringent compounds include aluminum chloride, aluminum chlorhydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorhydrates and aluminum-zirconium chlorohydrates, such as aluminum zirconium tetrachlorohydrex glycine which is commercially available as Rezal 36 GP Superultrafine (Reheis), and Reach AZP 908 (Reheis). The organometallic astringent compounds tend to have lower densities which are advantageous for purposes of density matching of the organic matrix phase and dispersed particle phase in a pharmaceutical product.

Mixtures of the above skin actives may be incorporated into the present invention.

Alkyl Amides of Di- and/or Tri-basic Carboxylic Acids

Another essential component of the present invention are gelling agents in the form of alkyl amides of di- and/or tri-basic carboxylic acids or anhydrides. Alkyl amides suitable for use in the present invention generally have the formula:

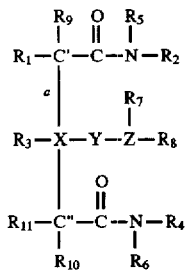

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nil, nitrogen, aryl or –(CH$_2$)$_n$– where n is an integer from 1 to 6, preferably –(CH$_2$)$_n$– where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl; and j) "a" is a double or single bond provided:
  (i) when X is nil, Y, Z, $R_3$, $R_7$ and $R_8$ are nil, C' is bonded directly to C" and $R_1$ is not a hydrogen;
  (ii) when X and Z are not nil and Y is nil, X is directly bonded to Z;

(iii) when Z is nil, a hydrogen or a hydroxy, $R_7$ and $R_8$ are nil; and (iv) when "a" is a double bond, $R_3$ and $R_9$ are nil.

Alkyl amides of di- and tri-basic carboxylic acids or anhydrides suitable for use in the present invention include alkyl amides of citric acid, tricarballylic acid, aconitic acid, nitrilotriacetic acid, succinic acid and itaconic acid such as 1,2,3-propane tributylamide, 2-hydroxy-1,2,3-propane tributylamide, 1-propene-1,2,3-trioctylamide, N,N',N"-tri (acetodecylamide)amine, 2-dodecyl-N,N'-dihexylsuccinamide, and 2-dodecyl-N,N'-dibutylsuccinamide. Preferred for use in the present invention are alkyl amides of di-carboxylic acids such as di-amides of alkyl succinic acids, alkenyl succinic acids, alkyl succinic anhydrides and alkenyl succinic anhydrides, more preferably 2-dodecyl-N,N'-dibutylsuccinamide.

The alkyl amide gelling agents, preferably, have opposing and substantially parallel terminal chains extending outward from the gelling agent backbone. Without being limited by theory, it is believed that this spacial arrangement, or "tuning fork" structural configuration, facilitates the formation of networks essential to the formulation of gel or stick compositions. By the phrase "tuning fork configuration", as used herein means any configuration resembling an article/or implement having a handle portion which extends longitudinally at one end to form two prongs. It is also preferred that the terminal chains be linked to the gelling agent backbone by means of acylamide linkages wherein the acyl portion of the acyl-amide linkage is directly attached to the gelling agent backbone.

The alkyl amides of the present invention are synthesized using either of the following one or two step reaction procedures.

The one step procedure involves direct amidation of the di- or tri-basic organic acid or anhydride with the appropriate alkyl amine under reaction temperatures typically at or near the boiling point of the alkyl amine, preferably from about 30° C. to about 200° C., followed by removal of excess amine. Certain reactions, do to their exothermic nature, may not require external heating.

The two step procedure involves esterification of the di- or tri-basic organic acid or anhydride with methanol using a boron trifluoride or other Lewis Acid catalyst at a temperature of from about 30° C. to about 100° C. followed by removal of the excess methanol and catalyst. The resulting trimethyl ester is then amidated as described in the one step process above using the appropriate alkylamine followed by removal of excess amine. Preferably, the alkyl amides of the present invention are nonpolymeric.

When the alkylamide of the present invention is included at lower levels in the composition, a gel is formed. At higher levels, or when other gelling agents are included in the composition, the hardness of the composition is increased, so as to form a hard stick. The alkyl amides of di- and tribasic carboxylic acids are preferably present at a concentration of from about 0.1% to about 25%, more preferably from about 1% to about 15%, most preferably from about 1% to about 10%.

Anhydrous Liquid Carrier

The pharmaceutical compositions of the present invention comprise an anhydrous liquid carrier for the alkylamide of the present invention, wherein the pharmaceutical carrier comprises one or more anhydrous liquids which each or collectively have a solubility parameter of from about 3 to about 20 $(cal/cm^3)^{1/2}$, preferably from about 5 to about 16 $(cal/cm^3)^{1/2}$, more preferably from about 5 to about 11 $(cal/cm^3)^{1/2}$. The anhydrous carrier is a liquid under ambient conditions.

Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Pharmaceuticals and Toiletries 47–69, October 1988; and C. D. Vaughan, "Using Solubility Parameters in Pharmaceuticals Formulation", 36 J. Soc. Pharmaceutical Chemists 319–333, September/October, 1988, which descriptions are incorporated herein by reference.

Concentrations of the anhydrous liquid carrier in the pharmaceutical composition will vary with the type of carrier selected, the type of gelling agent used in combination with the carrier, and the solubility of the selected gelling agent in the selected carrier, and so forth. Preferred concentrations of the anhydrous liquid carrier ranges from about 10% to about 80%, preferably from about 30% to about 70%, more preferably from about 45% to about 70%, by weight of the composition.

The anhydrous liquid carrier preferably comprises one or more anhydrous liquids suitable for topical application to human skin, which carrier or combination of liquid carriers are liquid under ambient conditions. The term "anhydrous" as used herein means that the pharmaceutical gel compositions of the present invention, and the essential or optional components thereof other than the pharmaceutically acceptable actives, are substantially free of added or free water. From a formulation standpoint, this means that the pharmaceutical gel compositions of the present invention preferably contain less than about 5%, preferably less than about 3%, more preferably less than about 1%, most preferably zero percent, by weight of free or added water, other than the water of hydration typically associated with the pharmaceutically acceptable actives prior to formulation. These anhydrous, liquid carriers may be organic or silicone-containing, volatile or non-volatile, polar or nonpolar, provided that the carrier can form a solution or other homogenous liquid or homogenous liquid dispersion with the selected gellant at the selected gellant concentration at a temperature of from about 28° C. to about 250° C., preferably from about 28° C. to about 100° C., more preferably about 28° C. to about 78° C. The anhydrous liquid carrier preferably has a low viscosity to provide for improved spreading performance on the skin.

The anhydrous liquid carrier preferably comprises a modified or organofunctional silicone carrier selected from the group consisting of polyalkylsiloxanes, polyalkyarylsiloxanes, polyestersiloxanes, polyethersiloxane copolymers, polyfluorosiloxanes, polyaminosiloxanes, and combinations thereof. These modified silicone carriers must be liquid under ambient conditions, and have a viscosity of less than about 100,000 centistokes, preferably less than about 500 centistokes, more preferably from about 1 centistoke to about 50 centistokes, and even more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

The modified silicone carriers suitable for use in the pharmaceutical compositions include, but are not limited to, compounds or materials as defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu ,e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone carriers for use in the pharmaceutical compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone carriers for use in the pharmaceutical compositions herein include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate)

Other nonlimiting examples of suitable modified silicone carriers for use in the pharmaceutical compositions herein include the following modified silicones available from Goldschmidt: Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); and Tegomer H-Si2111, H-Si2311, A-Si2120, A-Si2320, C-Si 2141, C-Si 2341, E-Si2130, E-Si2330, V-Si2150, V-Si2550, H-Si6420, H-Si6440, H-Si6460 (Alpha-Omega Dimethicone Copolymers).

Other nonlimiting examples of suitable modified silicone carriers for use in the pharmaceutical compositions herein include the following: Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-711, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris[tributoxysiloxy] methylsilane); silicone copolymer F-754 (dimethicone copoly from SWS Silicones); and combinations thereof.

The anhydrous liquid carrier preferably comprises one or more volatile carriers, optionally in combination with one or more non-volatile carrier. In this context, the term "volatile" refers to carriers having a measurable vapor pressure under ambient conditions, and the term "non-volatile" refers to carriers which do not have a measurable vapor pressure under ambient conditions. These volatile silicone carriers may be cyclic, linear or branched chain silicones having the requisite volatility defined herein. Non-limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

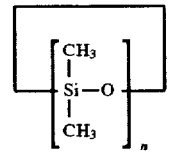

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1 173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof.

The anhydrous liquid carrier may also comprise a non-volatile silicone carrier other than or in addition to the preferred modified silicone carriers described hereinbefore. These non-volatile silicone carriers are preferably linear silicones which include, but are not limited to, those which conform to either of the formulas:

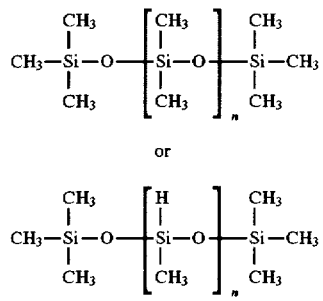

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The anhydrous liquid carrier may also comprise fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress ® PFPE oils, and the series fluorosurfactants from Dupont Performance Chemicals under the trade name Zonyl ® Fluorosurfactants.

Suitable organic liquid carrier include polar or nonpolar, saturated or unsaturated, substituted or unsubstituted, branched or linear or cyclic, organic compounds that are also liquid under ambient conditions. These carriers include hydrocarbon oils, alcohols, organic esters and ethers that are liquid under ambient conditions. Preferred organic carriers include mineral oil and other hydrocarbon oils, some examples of which are described in U.S. Pat. No. 5,019,375, issued to Tanner et al. on May 28, 1991, which description is incorporated herein by reference. Other suitable organic liquid carriers include Permethyl 99A, Permethyl 101A (Permethyl available from Persperse Corp.), Isopar series of materials (available from Exxon), isohexadecane, diisopropyl adipate, butyl stearate, isododecane, light mineral oil, petrolatum and other similar materials.

The anhydrous liquids carrier is preferably, substantially free of polar, water immiscible, organic solvents. In this context, "substantially free" means that the gel solid compositions preferably contain less than 7%, more preferably less than about 3%, even more preferably zero percent, by weight of an anhydrous organic polar solvent. These solvents are liquid under ambient conditions and include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Examples of some anhydrous liquid, polar organic solvents are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

As discussed previously, the compositions of the present invention can be formulated as either a gel or a gel stick. These gels or gel sticks take the form of facial or body gels, soft gels, creams, lotions, roll-on compositions, bar soaps, lip balms, facial moisturizers, sunscreens, anti-acne preparations, topical analgesics, antiperspirants, and deodorants. It is difficult to quantitatively distinguish between a pharmaceutical "gel" and a pharmaceutical "stick". For example, note the discussion in the article by Schmolka, "Gel Pharmaceuticals", in Pharmaceuticals &. Toiletries, Vol. 99 (November 1984), pp. 69–76. Generally, a gel is more viscous than a liquid, or than a paste which fails to retain its shape. It is not as rigid as a stick. Typically, it is understood that gels are soft, deformable products while sticks are free-standing solids.

OPTIONAL COMPONENTS

Optionally, the pharmaceutical compositions of the present invention may further incorporate moisturizers and/or skin protectants. Suitable cosmetic compositions include gel, bar soap, soft gel, cream, makeup, lotion, roll-on, facial moisturizer, or gel stick and the like. Useful moisturizers and/or skin protectants are disclosed in the Federal Register Vol. 48, No. 32 and include aloe vera, allantoin, aluminum hydroxide gel, bismuth subnitrate, boric acid, calamine, cocoa butter, corn starch, dimethicone, glycerin, lanolin, kaolin, live yeast cell derivative, petrolatum, shark liver oil, sodium bicarbonate, sulfur, tannic acid, white petrolatum, zinc acetate, zinc carbonate and zinc oxide and mixtures thereof. The skin protectant and/or moisturizer preferably comprises from about 0.001% to about 2%, more preferably from about 0.01% to about 1% of the pharmaceutical composition.

Other ingredients conventionally incorporated into pharmaceutical gels and/or sticks may also be included. As for the various other ingredients which can be incorporated, attention is directed to such optional components as hardeners, strengtheners, chelating agents, colorants, perfumes, emulsifiers and fillers. These other optional components are further described in U.S. Pat. No. 3,255,082 to Barton; U.S. Pat. No. 4,049,792 to Elsnau; U.S. Pat. No. 4,137,306 to Rubino, et al; U.S. Pat. No. 4,279,658 to Hooper, et al; Canadian Patent 1,164,347 which issued to Beckmeyer et al.; European Patent Application 117,070 which published on Aug. 29, 1984; and Geria, "Formulation of Stick Antiperspirants and Deodorants", Pharmaceuticals and Toiletries, 99: 55–60 (1984), all of which are herein incorporated by reference in their entirety.

Emulsifiers are particularly useful in the present invention. These emulsifiers include non-ionic surfactants useful for forming water-in-oil emulsions. The level of emulsifiers used in the present invention is typically less than about 10%, preferably less than about 5%. Examples of these emulsifiers include polyoxyethylene ethers of fatty alcohols, and polyoxyethylene-polysiloxane copolymers. Such emulsifiers are disclosed by EPO Application 373,424 Raleigh et al., and U.S. Ser. No. 530,671, Cedeno et al., filed Jul. 2, 1991, all of which are herein incorporated by reference in their entirety.

Preferably, when the compositions of the present invention are in the form of a solid emulsion, the compositions include a surfactant. This ensures that the discontinuous phase stays dispersed upon cooling of the composition to form the gel. Preferred for use herein are surfactants which are easily rinsed from the skin.

Thickeners are also useful in the present invention. Their selection and the level at which they are used should be so as not to significantly affect the aesthetics of the gel compositions. Typical levels of thickeners are at levels of less than about 5%. Examples of said thickeners are disclosed in U.S. Pat. No. 4,985,238, Tanner et al., issued Jan. 15, 1991; herein incorporated by reference in its entirety. These thickeners include wax-like materials such as beeswax, cerasin, hydrogenated castor oil, synthetic waxes such as Fisher Tropsch waxes, microcrystalline waxes, polyethylene waxes, and mixtures thereof.

In addition to the alkylamide gelling agent described above, the compositions of the present invention may also incorporate other gelling agents. Suitable additional gelling agents are disclosed in U.S. Pat. No. 5,429,816 to Hofrichter et al., issued Jul. 4, 1995, herein incorporated by reference in its entirety. Gelling agents included therein include those having the formula:

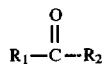

wherein $R_1$ is $OR_2$ or $NR_2R_3$ wherein $R_2$ and $R_3$ are, independently or together, a hydrogen, an aryl, a siloxane, a saturated or unsaturated, substituted or unsubstituted, straight, branched, or cyclic $C_1$–$C_{22}$ alkyl, $C_1$–$C_{22}$ alkoxy, $C_1$–$C_{22}$ alkyl substituted aryl, or $C_1$–$C_{22}$ alkyl substituted aryl radical and wherein $R_2$ is a saturated or unsaturated, substituted or unsubstituted, straight or branched chain $C_1$–$C_{36}$ alkoxy. Preferred gelling agents from among this group include 12-hydroxystearic acid, 12-hydroxystearic acid methyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, 12-hydroxylauric acid, 16-hydroxyhexadecanoic acid, derivatives thereof and mixtures thereof.

Also in U.S. Pat. No. 5,429,816 are gelling agents having the formula:

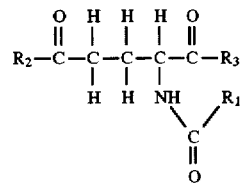

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms. Preferred gelling agents from among this group include N-lauroyl-glutamic acid diethyl amide, N-lauroyl-glutamic acid dibutyl amide, N-lauroylglutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof. Mixtures of the above described additional gelling agents may also be incorporated into the present invention.

Mixtures of these gelling agents may also be incorporated into the present invention.

Particulate and filler materials may also be included in the present compositions. These materials are typically used at levels of from about 0.5% to about 5%, preferably not more than about 3%. Such materials are disclosed in U.S. Pat. No. 5,019,375, Tanner et al., issued May 28, 1991, herein incorporated by reference in its entirety. Suitable filler materials include collodial silica (such as Cab-O-Sil, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in pharmaceutical sticks is disclosed in U.S. Pat. No. 4,126, 679, Davy et al., issued Nov. 21, 1987, incorporated by reference in its entirety. Examples of other particulate materials include particulate hydrophilic polymers such as cellulose ether polymers, modified starches, polyamides, and polypeptides.

A wash-off agent may be utilized to improve the ease with which the ingredients—particularly the gelling agent and the non-polar, non-volatile oils—may be washed off. The wash-off agent is highly preferably a non-liquid. The wash-off agent is typically in the pharmaceutical compositions in an amount from about 0.1% to about 10%.

Typical wash-off agents are non-liquids selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$-preferably, the polyoxyethylene ethers-wherein: $R_1$ and $R_2$ are the same or different alkyl, alkenyl, or aromatic hydrocarbon radical which may be substituted or unsubstituted—preferably an alkyl radical—having from about 4 to about 22 carbon atoms; and n is from about 2 to about 80.

Preferred examples of such wash-off agents include: ceteth-2 through ceteth-30, steareth-2 through steareth-30, ceteareth-2 through ceteareth-30, PEG-2 stearate through PEG-30 stearate, PEG-12 isostearate, PEG-16 hydrogenated castor oil, PEG-40 hydrogenated castor oil, and PEG-20 glyceryl stearate; more preferably, ceteareth-20, steareth-21, PEG-20 stearate, and PEG-16 hydrogenated castor oil; and most preferably, ceteareth-20.

Methods Of Manufacture

The present invention may be made by using any of the typical methods known to those skilled in the art, and disclosed in Gels and Sticks Formulary, 99 Pharmaceuticals & Toiletries 77–84, 1984; herein incorporated by reference. Methods found particularly useful follow below:

Combine the gelling agent and the carrier into a vessel equipped with a heat source. Heat the mixture to between about 80° C. and about 130° C. with stirring, until the mixture forms a homogeneous, molten solution. Preferably, the homogeneous, molten solution is allowed to cool to a mixing temperature; typically between about 65° C. and 120° C. Alternatively, the mixture may simply be heated to the mixing temperature until the mixture forms a homogeneous, molten solution. This alternative method, however, typically takes longer than simply overheating and then cooling. Add the topical skin active(s) and other ingredients, such as fragrances and colors, into the homogeneous, molten solution in the above vessel with stirring. Allow the mixture to cool until it begins thickening and then pour the mixture into containers allowing them to cool to ambient temperature. Although not preferred, the topical skin active(s) may alternatively be added along with the gelling agent and the liquid base material in the first step.

Methods For Use

The present invention provides methods for preventing perspiration and malodor associated with human perspiration. These methods comprise applying to the skin of a human a safe and effective amount of the pharmaceutical gel of the present invention. The term "a safe and effective amount" as used herein, is an amount which is effective in eliminating or substantially reducing malodor associated with human underarm perspiration while being safe for human use at a reasonable risk/benefit ratio. Typically, the safe and effective amount used is from about 0.1 gram to about 1.0 gram per surface area of skin.

EXAMPLES

The following examples further describe and demonstrate embodiments within the scope of the present invention. These examples are solely for the purpose of illustration and are not to be construed as limitations of the present invention as many variations are possible without departing from the spirit or scope thereof. The levels of the components in the examples below are expressed by total weight of the composition.

Table 1 includes examples of pharmaceutical gel-solid stick compositions incorporating the alkylamide gelling agents of the present invention. The compositions are formed by combining and mixing the ingredients of each column using conventional technology.

TABLE 1

| Component | Example I | Example II | Example III | Example IV | Example V |
|---|---|---|---|---|---|
| Cyclomethicone[1] | 71.0 | 71.5 | 46.0 | 62.0 | 29.25 |
| Octyldodecanol[2] | 18.0 | 18.0 | 14.0 | — | — |
| Petrolatum 3 | — | — | — | — | 55.0 |
| $C_{12}$–$C_{15}$ Alkyl Benzoate[5] | — | — | — | 20.0 | — |
| 12-Hydroxystearic Acid[4] | — | — | — | 13.0 | — |
| 1,2,3-Propane tributylamide | 10.0 | 5.0 | — | — | 15.0 |
| 2-Hydroxy-1,2,3-propane tributylamide | — | — | 25.0 | — | — |
| 1-Propene-1,2,3-trioctylamide | — | — | — | 3.0 | — |
| 2-Dodecyl-N,N'-dihexylsuccinamide | — | 5.0 | — | — | — |
| Salicylic Acid | 1.0 | — | — | 2.0 | — |
| Glycolic Acid | — | 0.5 | — | — | — |
| Clotrimazole | — | — | 2.0 | — | — |
| Triclosan | — | — | — | — | 0.75 |

[1]Dow Corning 245 Fluid; General Electric SF-1202
[2]Jarchem Jarcol I-20
[3]Witco White Perfecta
[4]Acme Hardesty
[5]Finsolv TN; Finetex Table 2 includes examples of pharmaceutical soft gel compositions incorporating the alkylamide gelling agents of the present invention. The compositions are formed by combining and mixing the ingredients of each column using conventional technology.

TABLE 2

| Component | Example VI | Example VII | Example VIII | Example IX | Example X |
|---|---|---|---|---|---|
| Cyclomethicone[1] | 80.0 | 80.5 | 76.0 | 74.0 | — |
| Octyldodecanol[2] | 18.0 | 18.0 | — | 20.0 | — |
| Petrolatum[3] | — | — | — | — | — |
| $C_{12}$–$C_{15}$ Alkyl Benzoate[5] | — | — | 20.0 | — | — |
| 12-Hydroxystearic Acid[4] | — | — | — | 3.0 | — |
| Diethyl Pthalate | — | — | — | — | 98.25 |
| 1,2,3-Propane tributylamide | 1.0 | 0.5 | — | — | 1.0 |
| 2-Hydroxy-1,2,3-propane tributylamide | — | — | 2.0 | — | — |
| 1-Propene-1,2,3-trioctylamide | — | — | — | 1.0 | — |
| 2-Dodecyl-N,N'-dihexylsuccinamide | — | 0.5 | — | — | — |
| Salicylic Acid | 1.0 | — | — | 2.0 | — |
| Glycolic Acid | — | 0.5 | — | — | — |
| Clotrimazole | — | — | 2.0 | — | — |
| Triclosan | — | — | — | — | 0.75 |

[1]Dow Corning 245 Fluid; General Electric SF-1202
[2]Jarchem Jarcol I-20
[3]Witco White Perfecta
[4]Acme Hardesty
[5]Finsolv TN; Finetex

What is claimed is:

1. A pharmaceutical composition comprising:

A.) a safe and effective amount of at least one pharmaceutical active;

B.) a gellant of the formula:

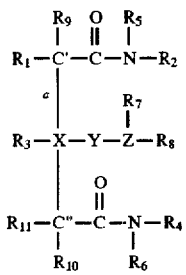

a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl;

e) $R_9$ is nil or hydrogen;

f) $R_{10}$ and $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl;

g) X is nil, nitrogen, aryl or –(CH$_2$)$_n$– where n is an integer from 1 to 6;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl; and j) "a" is a double or single bond provided:
  (i) when X is nil, Y, Z, $R_3$, $R_7$ and $R_8$ are nil, C' is bonded directly to C" and $R_1$ is not a hydrogen;
  (ii) when X and Z are not nil and Y is nil, X is directly bonded to Z;
  (iii) when Z is nil, a hydrogen or a hydroxy, $R_7$ and $R_8$ are nil; and
  (iv) when "a" is a double bond, $R_3$ and $R_9$ are nil; and C.) an anhydrous liquid carrier.

2. A pharmaceutical composition according to claim 1, wherein the pharmaceutically acceptable active selected from the group consisting of a deodorant active, an analgesic, an exfoliant a sunscreen agent, a vitamin, an anti-dandruff agent, an antioxidant or radical scavenger, a hormone and mixtures thereof.

3. A pharmaceutical composition according to claim 1, wherein the pharmaceutical composition comprises from about 0.1% to about 25% of the gelling agent.

4. A pharmaceutical composition according to claim 3, wherein the gelling agent is selected from the group consisting of alkyl amides of citric acid, tricarballylic acid, aconitic acid, nitrilotriacetic acid, alkylamides of alkyl succinic acid, alkylamides of alkenyl succinic acid and anhydrides thereof.

5. A pharmaceutical composition according to claim 4, further comprising from about 1% to about 15% by weight of a secondary gelling agent having the formula:

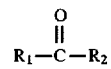

wherein $R_1$ is $OR_2$ or $NR_2R_3$ wherein $R_2$ and $R_3$ are, independently or together, a hydrogen, an aryl, a siloxane, a saturated or unsaturated, substituted or unsubstituted, straight, branched, or cyclic $C_1$–$C_{22}$ alkyl, $C_1$–$C_{22}$ alkoxy, $C_1$–$C_{22}$ alkyl substituted aryl, or $C_1$–$C_{22}$ alkyl substituted aryl radical and wherein $R_2$ is a saturated or unsaturated, substituted or unsubstituted, straight or branched chain $C_1$–$C_{36}$ alkoxy.

6. A pharmaceutical composition according to claim 5, wherein the secondary gelling agent is selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, 12-hydroxylauric acid, 16-hydroxyhexadecanoic acid, derivatives thereof and mixtures thereof.

7. A pharmaceutical composition according to claim 1, further comprising an additional gelling agent having the formula:

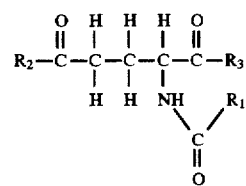

wherein $R_1$ is an alkyl, aryl, arylalkyl radical is branched, linear or cyclic and has from about 6 to about 22 carbon atoms; and $R_2$ and $R_3$ are the same or different alkyl, aryl, arylalkyl ester radical or alkyl, aryl, arylalkyl amide radical, in which the moiety is branched, linear or cyclic and has from about 2 to about 20 carbon atoms.

8. A pharmaceutical composition according to claim 7, wherein the additional gelling agent is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoylglutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof.

9. A pharmaceutical composition according to claim 1, wherein the pharmaceutical carrier is an anhydrous liquid.

10. A pharmaceutical composition according to claim 9, wherein the pharmaceutical carrier has a solubility parameter of from about 3 to about 20 $(cal/cm^3)^{1/2}$.

11. A pharmaceutical composition according to claim 10, wherein the anhydrous carrier is selected from the group consisting of: nonpolar, volatile oils; relatively polar, non-volatile oils; nonpolar, non-volatile oils; and mixtures thereof.

12. A pharmaceutical composition according to claim 11, wherein the nonpolar, volatile oils are selected from the group consisting of non-volatile polysiloxanes, paraffinic hydrocarbon oils, and mixtures thereof.

13. A pharmaceutical composition according to claim 12, wherein the non-volatile polysiloxanes are selected from the group consisting of polyalkylsiloxanes, polyarylsiloxanes, polyalkylarylsiloxanes, poly-ethersiloxane copolymers, polyfluorosiloxane, polyaminosiloxane and mixtures thereof.

14. A pharmaceutical composition according to claim 12, wherein the paraffinic hydrocarbon oil is selected from the group consisting of mineral oils, petrolatums, isodecanes, permethyls, isohexadecanes, isododecane, isoparaffins.

15. A pharmaceutical composition according to claim 1, wherein the carrier is in the form of a lip balm, gel, bar soap, soft gel, cream, lotion, roll-on, facial moisturizer, gel stick, sunscreen preparation, anti-acne preparation, topical analgesic preparation or deodorant.

16. A pharmaceutical composition according to claim 15, wherein the carrier forms a gel stick.

17. A pharmaceutical composition according to claim 15, further comprising a moisturizer or protectant.

18. A pharmaceutical composition according to claim 17 wherein the moisturizer or protectant is selected from the group consisting of aloe vera, allantoin, aluminum hydroxide gel, bismuth subnitrate, boric acid, calamine, cocoa butter, corn starch, dimethicone, glycerin, lanolin, kaolin, live yeast cell derivative, petrolatum, shark liver oil, sodium bicarbonate, sulfur, tannic acid, white petrolatum, zinc acetate, zinc carbonate and zinc oxide and mixtures thereof.

19. A pharmaceutical composition, comprising:

a.) a safe and effective amount of at least one pharmaceutical active;

b.) a non-triglyceride gelling agent compound, comprising:

i.) a $C_2$–$C_{12}$ linear backbone having terminal hydrogen bonding functional groups, each hydrogen bonding functional group carrying thereon a non-polymeric, organic side chain; and ii.) an additional non-polymeric, organic side chain attached to the backbone by an acyl-amide functional group such that the acyl portion of the acylamide functional group attaches to the backbone wherein the side chains of the hydrogen bonding functional groups are disposed on the same axial side of the backbone such the additional side chain is disposed on a planar side opposite the side chains of the hydrogen bonding functional groups; and c.) an anhydrous liquid carrier.

20. An antiperspirant composition according to claim 17, wherein the side chains of the hydrogen bonding functional group are attached to the hydrogen bonding functional group by acyl-amide functional groups such that the acyl portion of the acyl-amide functional group attaches to the hydrogen bonding functional group.

* * * * *